United States Patent [19]

Riordan et al.

[11] Patent Number: 5,756,524
[45] Date of Patent: May 26, 1998

[54] ANILIDE DERIVATIVES AS FUNGICIDES

[75] Inventors: Peter Dominic Riordan, Dunmow; Susan Elizabeth Osbourn, Cambridge, both of England; Ian Kenneth Boddy, Hamilton, New Zealand

[73] Assignee: Agrevo UK Limited, Cambridge, England

[21] Appl. No.: 714,149

[22] PCT Filed: Mar. 16, 1995

[86] PCT No.: PCT/GB95/00570

§ 371 Date: Sep. 18, 1996

§ 102(e) Date: Sep. 18, 1996

[87] PCT Pub. No.: WO95/25723

PCT Pub. Date: Sep. 28, 1995

[30] Foreign Application Priority Data

Mar. 18, 1994 [GB] United Kingdom ............... 9405347

[51] Int. Cl.$^6$ ............... C07F 3/14; C07D 213/64; A01N 43/40

[52] U.S. Cl. ............... 514/346; 514/188; 546/6; 546/292; 546/288; 546/289

[58] Field of Search ............... 546/6, 288, 289, 546/292; 514/344, 345, 348, 351, 355, 188

[56] References Cited

FOREIGN PATENT DOCUMENTS 2417216 11/1975 Germany.

OTHER PUBLICATIONS

Chemical Abstracts, vol. 77(17)abst.No. 114,078(b), Oct. 23, 1972.

Chemical Abstracts, vol. 84(7)abst.No. 39,707v Feb. 16, 1976.

Chemical Abstracts, vol. (3).abst.No. 15765u, Jan. 16, 1978.

O. Kirino et al., "Fungicidal Activity of N-benzoylanthranilates and Related Compounds", Agricultural and Biological Chemistry, vol. 44, No. 9, 1980, Tokyo, Japan, pp. 2143–2147.

*Primary Examiner*—Alan L. Rotman
*Attorney, Agent, or Firm*—Ostrolenk, Faber, Gerb & Soffen, LLP

[57] ABSTRACT

A compound of formula I

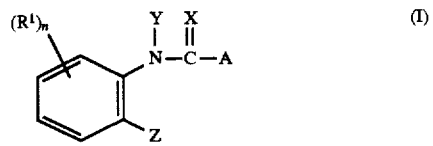

X is O or S;
A is 6-alkoxy-3-pyridyl optionally substituted by halogen;
Y is hydrogen or alkyl;
$R^3$ is alkyl or a metal salt complex thereof. This invention contains fungicidal compositions and are used to combat cytopathogenic fungi.

17 Claims, No Drawings

ANILIDE DERIVATIVES AS FUNGICIDES

This application is a 371 of PCT/GB 95/00570 filed 03/16/95.

FIELD OF THE INVENTION

This invention relates to new derivatives of anthranilic acid useful as fungicides.

PRIOR ART

DE 2417216 discloses inter alia, N-phenylcarbamoylpyridine compounds as fungicides in which the pyridine is substituted by chlorine and the phenyl can be substituted by carboxy. In *J. Agric. Biol. Chem* 44(9), 2143, 1980, certain N-benzoylanthranilates are described as fungicides. Similar compounds are disclosed in GB 1,563, 664 and Japanese Kokai 53130655. We have found that certain novel anthranilic acid derivatives also have valuable fungicidal activity and also have advantages over compounds disclosed in these publications.

DISCLOSURE OF THE INVENTION

According to the invention there is provided a compound of formula I

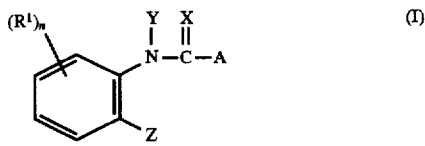

X is O or S;

A is a 6 membered heteroaryl group comprising at least one nitrogen atom, which is optionally substituted by one or more of the group $R^2$;

$R^1$ is alkyl, cycloalkyl, cycloalkenyl, alkenyl, alkynyl, $Y^1$—X— or amino, (each of which is optionally substituted), halogen, cyano, nitro, acyl, acyloxy, optionally substituted heterocyclyl or optionally substituted phenyl; or two adjacent groups together with the carbon atoms to which they are attached can form an optionally substituted benzo ring;

$R^2$ has the same meaning as $R^1$ or two adjacent groups together with the carbon atoms to which they are attached can form an optionally substituted heterocyclic ring;

Y is alkyl, cycloalkyl, cycloalkenyl, alkenyl or alkynyl, each of which is optionally substituted, hydrogen or acyl;

$Y^1$ has the same meaning as Y or is optionally substituted phenyl or optionally substituted heterocyclyl Z is C(=$X^1$)—$X^2$—$R^3$, cyano, optionally substituted heterocyclyl, —C($R^5$)=N—$OR^6$ or —C($R^5$)=N—$NR^6R^7$;

$R^3$ is alkyl, cycloalkyl, cycloalkenyl, alkenyl, alkynyl, phenyl or heterocyclyl, each of which is optionally substituted, hydrogen or an inorganic or organic cationic group.

$X^1$ and $X^2$, which may be the same or different, are O or S;

$R^5$, $R^6$ and $R^7$, which may be the same or different, are alkyl, cycloalkyl, cycloalkenyl, alkenyl, alkynyl, phenyl or heterocyclyl, each of which is optionally substituted or hydrogen or $R^6$ and $R^7$ together with the atom(s) to which they are attached can form a ring;

n is 0 to 4, together with complexes with metal salts, as well as salts with bases of compounds which are acids and salts with acids of compounds which are bases, with the proviso that when Y is hydrogen and i) when Z is carboxy, methoxycarbonyl or ethoxycarbonyl ring A is not unsubstituted pyridyl or pyrazinyl; and ii) when Z is carboxy and n is 0, A is not 2-chloro-3-pyridyl, 6-(2-diethylaminoethoxy)-3-pyridyl or a 2-pyridyl group.

Alkyl groups are preferably of 1 to 20, eg 1 to 6, carbon atoms. Alkenyl and alkynyl groups are generally of 3 to 6 carbon atoms. Cycloalkyl or cycloalkenyl groups are preferably of 3 to 8 carbon atoms.

Substituents, when present on any alkyl, cycloalkyl, cycloalkenyl, alkenyl or alkynyl moiety include halogen, azido, cyano, optionally substituted alkoxy, optionally substituted alkylthio, hydroxy, nitro, optionally substituted amino, acyl, acyloxy, optionally substituted phenyl, optionally substituted heterocyclyl, optionally substituted phenoxy and optionally substituted heterocyclyloxy.

Cycloalkyl or cycloalkenyl groups may also be substituted by alkyl.

Substituents when present on any phenyl group are usually one or more of the same groups as defined for $R^1$.

The term heterocyclyl includes both aromatic and non-aromatic heterocyclyl groups. Heterocyclyl groups are generally 5, 6 or 7-membered rings containing up to 4 hetero atoms selected from nitrogen, oxygen and sulfur. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, triazinyl, thiazolinyl, benzimidazolyl, tetrazolyl, benzoxazolyl, imidazopyridinyl, 1,3-benzoxazinyl, 1,3-benzothiazinyl, oxazolopyridinyl, benzofuranyl, quinolinyl, quinazolinyl, quinoxalinyl, sulfolanyl, dihydroquinazolinyl, benzothiazolyl, phthalimido, benzofuranyl, azepinyl, oxazepinyl, thiazepinyl, diazepinyl and benzodiazepinyl.

Heterocyclyl groups may themselves be substituted for example as for phenyl.

Amino groups may be substituted for example by one or two optionally substituted alkyl or acyl, or two substituents can form a ring, preferably a 5 to 7-membered ring, which may be substituted and may contain other heteroatoms, for example morpholine, thiomorpholine, or piperidine.

The term acyl includes the residue of sulfur and phosphorus-containing acids as well as carboxylic acids. Examples of acyl groups are thus —$COR^5$, —$COOR^5$, —$CXNR^5R^6$, —CON ($R^5$) $OR^6$, —$COONR^5R^6$, —CON ($R^5$)$NR^6R^7$, —$COSR^5$, —$CSSR^5$, —S(O)$_pR^5$, —S(O)$_2OR^5$, —S(O)$_pNR^5R^6$, —P(=X) ($OR^5$) ($OR^6$), —CO—$COOR^5$, where $R^5$, $R^6$ and $R^7$ are as defined previously, or $R^6$ and $R^7$ together with the atom(s) to which they are attached can form a ring, p is 1 or 2 and X is O or S.

It is generally preferred that A is a pyridine, (especially 3-pyridyl), a pyrimidine (especially 5-pyrimidinyl), or a pyrazine ring. A may also be for example a tetrazine, pyridazine or triazine ring.

$R^2$ is preferably selected from halogen and alkoxy, especially methoxy.

$R^1$ is preferably selected from halogen, especially fluorine, and alkyl, especially methyl.

Z is preferably C(=$X^1$)—$X^2$—$R^3$. $X^1$ and $X^2$ are both preferably O and $R^3$ is generally alkyl, alkenyl or alkynyl, each of which is optionally substituted, and is especially methyl.

Y is preferably hydrogen, alkyl, especially methyl or acyl, especially alkanoyl or alkoxycarbonyl.

X is preferably O.

n is preferably 0.

Complexes of compounds of the invention are usually formed from a salt of formula $MAn_2$, in which M is a divalent metal cation, e.g. copper, manganese, cobalt, nickel, iron or zinc and An is an anion, e.g. chloride, nitrate or sulfate.

The compounds of the invention have activity against a wide range of pathogens of Deuteromycete, Ascomycete, Phycomycete and Basidiomycete origin, especially against fungal diseases of plants, e.g. mildews and particularly barley powdery mildew (*Erysiphe graminis*) cucumber powdery mildew (*Erysiphe cichoracaerum*) and vine downy mildews (*Plasmopara viticola* and *Uncinula necator*), rice blast (*Pyricularia oryzae*), cereal eyespot (*Pseudocercosporella herpotrichoides*), rice sheath blight (*Pellicularia sasakii*), grey mould (*Botrytis cinerea*), wheat brown rust (*Puccinia recondita*), late tomato or potato blight (*Phytophthora infestans*), apple scab (*Venturia inaequalis*) and glume blotch (*Leptosphaeria nodorum*). Some compounds may be active against only a few pathogens whereas others may have a broader spectrum of activity.

Some novel compounds of formula I have weak pesticidal activity but still have utility as intermediates and such compounds also form one aspect of the invention.

The compounds of the invention are generally formulated in conventional compositions used for fungicides. These compositions can contain one or more additional pesticides, for example compounds known to possess herbicidal, fungicidal, insecticidal, acaricidal or nematicidal properties.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl-aryl sulfonates such as alkyl-benzene sulfonates or lower alkylnaphthalene sulfonates, e.g. butyl-naphthalene sulfonate; salts of sulfonated naphthalene-formaldehyde condensates; salts of sulfonated phenol-formaldehyde condensates; or more complex sulfonates such as the amide sulfonates, e.g. the sulfonated condensation product of oleic acid and N-methyl taurine or the dialkyl sulfosuccinates, e.g. the sodium sulfonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl- 5-decyne-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a fumigant, a smoke, a dispersible powder, an emulsifiable concentrate or granules. Moreover it can be in a suitable form for direct application or as a concentrate or primary composition which requires dilution with a suitable quantity of water or other diluent before application.

As a dispersion, the composition comprises a compound of the invention dispersed in a liquid medium, preferably water. It is often convenient to supply the consumer with a primary composition which can be diluted with water to form a dispersion having the desired concentration. The primary composition can be provided in any one of the following forms. It can be a dispersible solution which comprises a compound of the invention dissolved in a water-miscible solvent with the addition of a dispersing agent. A further alternative comprises a compound of the invention in the form of a finely ground powder in association with a dispersing agent and intimately mixed with water to give a paste or cream which can if desired be added to an emulsion of oil in water to give a dispersion of active ingredient in an aqueous oil emulsion.

An emulsifiable concentrate comprises a compound of the invention dissolved in a water-immiscible solvent together with an emulsifying agent and which is formed into an emulsion on mixing with water.

A dusting powder comprises a compound of the invention intimately mixed with a solid pulverulent diluent, for example, kaolin.

A granular solid comprises a compound of the invention associated with similar diluents to those which may be employed in dusting powders, but the mixture is granulated by known methods. Alternatively it comprises the active ingredient adsorbed or absorbed on a pre-granular diluent, for example, Fuller's earth, attapulgite or limestone grit.

A wettable powder usually comprises the active ingredient in admixture with a suitable surfactant and an inert powder diluent such as china clay.

Another suitable concentrate, particularly when the product is a solid, is a flowable suspension concentrate which is formed by grinding the compound with water, a wetting agent and a suspending agent.

The concentration of the active ingredient in the composition of the present invention is preferably within the range of 1 to 30 percent by weight, especially 5 to 30 percent by weight. In a primary composition the amount of active ingredient can vary widely and can be, for example, from 5 to 95 percent by weight of the composition.

The compounds of the invention may be prepared in known manner, for example by reacting a compound of formula II.

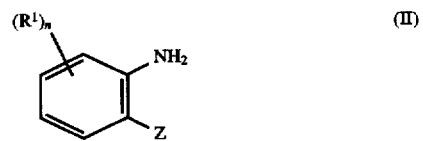

with a compound of formula III

where Q is a leaving group, preferably a halogen and especially chlorine, to give a compound of formula I, where X is O and Y is hydrogen. and if desired modifying this compound in known manner to give other compounds where X and/or Y have other desired values, and if desired modifying compounds of formula I in known manner to give compounds where $R^1$, $R^2$ and Z have other values.

The reaction between compounds II and III is generally carried out in the presence of a base, e.g. an organic tertiary amine and preferably in the presence of a solvent, e.g. an ether.

The compounds of formula II and III are either known or can be prepared in known manner.

The resulting compounds of formula I may be modified in known manner to give other compounds of formula I where one of the groups are modified to other desired groups.

For example an ester may be converted in known manner to a free acid or a salt.

Thio groups may be oxidised using a suitable oxidising agent, eg m-chloroperbenzoic acid, to give sulfinyl and sulfonyl groups.

Carbonyl groups may be converted to thiocarbonyl groups by sulfurising in known manner, e.g. using Lawesson's reagent or phosphorus pentasulfide.

Alkylsulfonyl groups on ring A may be replaced by a suitable nucleophile such as an aryloxy or arylthio group by reaction with the appropriate hydroxy or mercapto compound.

The invention is illustrated in the following Examples. Structures of isolated novel compounds were confirmed by elemental and/or other appropriate analyses. Temperatures are in °C.

Example 1

Triethylamine (28.4 g) was added to a solution of 6-chloronicotinic acid (40 g) in dry dichloromethane (900 ml). The mixture was cooled in an ice bath and methyl chloroformate (26.8 g) was added dropwise. The mixture was stirred at room temperature overnight, washed in turn with water, aqueous sodium hydrogen carbonate and brine. The organic phase was dried over magnesium sulfate, filtered and evaporated to give methyl 6-chloronicotinate.

10 g of this product was added to sodium methanolate (obtained from 1.61 g sodium and 100 ml dried methanol). The mixture was heated under reflux for 3 hours and allowed to stand at room temperature overnight. Aqueous potassium hydroxide (10 g in 30 ml water) was added and the mixture was heated under reflux for 8 hours. It was left to stand overnight at room temperature, evaporated and the residue added to water (120 ml). The mixture was acidified to pH 3 with hydrochloric acid. The precipitate was filtered and dried to give 6-methoxynicotinic acid, m.p. 175–177°.

This acid (6 g) was heated under reflux with an excess amount of thionyl chloride for 2 hours. The mixture was cooled, evaporated and the residue (comprising crude 6-methoxynicotinoyl chloride) was dissolved in dry tetrahydrofuran (10 ml). This solution was added dropwise to a solution of methyl anthranilate (6.22 g) and triethylamine (7.92 g) in dry tetrahydrofuran (200 ml). The mixture was stirred at room temperature overnight, evaporated and extracted with ethyl acetate. The extracts were washed with water, dried and evaporated and the residue purified by silica gel column chromatography to give methyl N-(6-methoxynicotinoyl) anthranilate, m.p. 121–3°. (compound 1) In a similar manner there was obtained methyl N-(2-methylthio-5-pyrimidinecarbonyl) anthranilate, m.p. 166–8°. (compound 1a)

Example 2

Sodium hydride (0.15 g of a 60% solution in oil) was added to a solution of the compound 1 from Example 1 (1 g) in dry tetrahydrofuran (25 ml) which had been cooled on an ice bath. The mixture was stirred for 20 minutes and then methyl iodide (0.44 ml) was added. The mixture was stirred at room temperature for 48 hours, evaporated and extracted with ethyl acetate. The extract was washed in turn with water and brine, dried over magnesium sulfate and evaporated. The residue was purified by silica gel column chromatography to give methyl N-(6-methoxynicotinoyl)-N-methylanthranilate), m.p. 68–70°. (compound 2)

Example 3

To a solution of compound 2 from Example 2 (0.6 g) in ethanol (20 ml) was added copper(II)chloride (0.134 g). The mixture was allowed to stand overnight, evaporated and the residue triturated with ethyl acetate to give bis-[methyl N-(6-methoxynicotinoyl)-N-methylanthranilate] copper(II) chloride complex, m.p. 196–8 °. (compound 3)

Example 4 m-Chloroperbenzoic acid (13.7 g) was added with stirring to a solution of compound 1a(6 g) in dichloromethane. The mixture was stirred overnight at room temperature, sodium sulfate added and extracted with dichloromethane. The extract was worked up to give methyl N-(2-methylsulfonyl-5-pyrimidinecarbonyl)anthranilate, m.p. 187–9°. (compound 4)

Example 5

Sodium hydride (0.24 g of a 60% dispersion in oil) was added to a solution of 2-mercaptopyridine (0.33 g) dissolved in dry dimethylformamide (20 ml). The mixture was stirred for half an hour at room temperature. A solution of compound 4 (1 g) in dry dimethylformamide (20 ml) was added dropwise with stirring. The mixture was stirred overnight at room temperature. It was cooled and quenched with methanol. The mixture was poured into water and made acidic with dilute hydrochloric acid. The precipitate was collected, dissolved in dichloromethane and the solution washed with brine and evaporated to give methyl N-[2-(2-pyridylthio)-5-pyrimidinecarbonyl]-anthranilate, mp. 145–147° (compound 5)

In a similar manner using potassium carbonate as the base instead of sodium hydride there was obtained methyl N-[2-(4-methoxyphenoxy)-5-pyrimidinecarbonyl]-anthranilate, as an oil (compound 5a).

Example 6

Compound 1 was heated with an equimolar amount of aqueous sodium hydroxide to give N-(6-methoxynicotinoyl)-anthranilic acid m.p. 224–3° (compound 6).

This compound in turn was treated with further sodium hydroxide to give sodium N-(6-methoxynicotinoyl)-anthranilate, m.p. >250° (compound 6a).

Example 7

Lawesson's reagent (2,4-bis(4-methoxyphenyl)-1,3-dithia-2,4-diphosphetane 2,4-disulfide; 5.09 g) was added to a solution of compound 1 (3 g) in dry tetrahydrofuran (100 ml). The mixture was stirred under nitrogen for 20 hours. More Lawesson's reagent (2.6 g) was added and the mixture heated under reflux for 13 hours, evaporated and the residue purified by silica gel column chromatography to give methyl N-(6-methoxy-3-pyridinethiocarbonyl)-anthranilate, m.p. 133–40°. (compound 7)

Example 8

In a similar manner to one of the processes disclosed in the previous Examples, the following compounds of formula I were obtained.

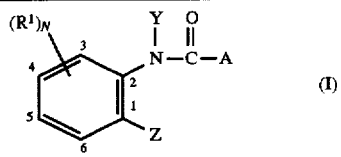

(I)

| Cpd | $(R^1)_n$ | Z | Y | A | m.p.(°) |
|---|---|---|---|---|---|
| 8 | — | COOMe | H | 6-EtO-3-pyridyl | 150–2 |
| 9 | — | COOEt | H | 6-MeO-3-pyridyl | 129–30 |
| 10 | — | COOEt | Me | 6-MeO-3-pyridyl | 91–2 |
| 11 | — | COOMe | —CH$_2$CN | 6-MeO-3-pyridyl | oil |
| 12 | — | COOMe | —COOMe | 6-MeO-3-pyridyl | gum |
| 13 | 3-Me | COOMe | H | 6-MeO-3-pyridyl | 111–2 |
| 14 | 5-Cl | COOMe | H | 6-MeO-3-pyridyl | 172–3 |
| 15 | 4,5-(MeO)$_2$ | COOMe | H | 6-MeO-3-pyridyl | 173–5 |
| 16 | — | COObenzyl | Me | 6-MeO-3-pyridyl | 110–3 |
| 17 | 5-Cl | COOMe | Me | 6-MeO-3-pyridyl | 89–91 |
| 18 | 4,5-(MeO)$_2$ | COOMe | Me | 6-MeO-3-pyridyl | 147–50 |
| 19 | 5-MeS | COOMe | H | 6-MeO-3-pyridyl | 135–7 |
| 20 | 5-MeS | COOMe | Me | 6-MeO-3-pyridyl | 78–80 |
| 21 | — | CN | H | 6-MeO-3-pyridyl | 163–6 |
| 22 | — | CN | Me | 6-MeO-3-pyridyl | 90.5–3 |
| 23 | — | COOMe | H | 5-MeO-2-pyrazinyl | 169–70 |
| 24 | 6-Me | COOMe | H | 6-MeO-3-pyridyl | 102.5–5 |
| 25 | — | COOMe | H | 5-Cl-6-MeO-3-pyridyl | 165–6 |
| 26 | — | COOMe | Me | 5-Cl-6-MeO-3-pyridyl | 110–2 |
| 27 | 6-Me | COOMe | Me | 6-MeO-3-pyridyl | 117.5–8.5 |
| 28 | — | COOPr$_i$ | H | 6-MeO-3-pyridyl | 107–9 |
| 29 | — | COOMe | H | 6-MeS-3-pyridyl | 102.5–5 |
| 30 | — | COOMe | Me | 6-EtO-3-pyridyl | oil |
| 31 | — | COOMe | H | 4,6-(MeO)$_2$-5-pyrimidinyl | 125–7 |
| 32 | — | COOMe | H | 5,6-(MeO)$_2$-2-pyrazinyl | 156–9 |
| 33 | — | COOMe | Me | 3-pyridyl | 86–8 |
| 34 | 4-NO$_2$ | COOMe | Me | 6-MeO-3-pyridyl | 110–2 |
| 35 | — | COOH | 2-F-benzyl | 6-MeO-3-pyridyl | 195–7 |
| 36 | 4-MeOCO | COOMe | Me | 6-MeO-3-pyridyl | 109–12 |
| 37 | — | COOMe | H | 5-(3-thienyl)-3-pyridyl | 149–50 |
| 38 | — | COOMe | Me | 6-NH$_2$-3-pyridyl | 119–22 |
| 39 | — | COOMe | H | 6-PrO-3-pyridyl | 15–7 |
| 40 | — | tetrazol-5-yl | Me | 6-MeO-3-pyridyl | 198–200 |
| 41 | — | COOMe | H | 6-MeCOO-3-pyridyl | 109–12 |
| 42 | 3-Cl | COOMe | H | 6-MeO-3-pyridyl | 106–10 |
| 43 | — | COOMe | H | 4-Cl-2-pyridyl | 158–60 |
| 44 | — | COOPr | H | 6-MeO-3-pyridyl | 107–9 |
| 45 | — | COOBu | H | 6-MeO-3-pyridyl | 57–60 |
| 46 | — | COOPr | Me | 6-MeO-3-pyridyl | 81.5–4 |
| 47 | — | COOBu | Me | 6-MeO-3-pyridyl | 72–6 |
| 48 | 3-Cl | COOMe | Me | 6-MeO-3-pyridyl | 84–7 |
| 49 | — | COO-allyl | H | 6-MeO-3-pyridyl | 98–9.5 |
| 50 | 4-Cl | COOMe | Me | 6-MeO-3-pyridyl | 98–100 |
| 51 | — | COOMe | —CH$_2$C≡CH | 6-MeO-3-pyridyl | 84.5–87 |
| 52 | — | C=N—NHMe \| Me | H | 6-MeO-3-pyridyl | 124–34 |
| 53 | — | C=N—OMe \| Me | H | 6-MeO-3-pyridyl | 115–6 |

-continued

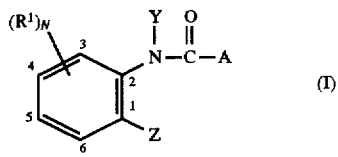
(I)

| Cpd | (R¹)ₙ | Z | Y | A | m.p.(°) |
|---|---|---|---|---|---|
| 54 | 4-F | COOMe | H | 6-MeO-3-pyridyl | 125–6 |
| 55 | — | COONH₄ | H | 6-MeO-3-pyridyl | 250–2 |
| 56 | 5,6-benzo | COOMe | H | 6-MeO-3-pyridyl | 157–61 |
| 57 | 4-CF₃ | COOMe | H | 6-MeO-3-pyridyl | 139–42 |
| 58 | — | COOMe | 4-CF₃-benzyl | 6-MeO-3-pyridyl | 111–3 |
| 59 | — | COOMe | H | 6-MeNH-3-pyridyl | 187–89 |
| 60 | — | COOMe | 2-Me-benzyl | 6-MeO-3-pyridyl | 112–4 |
| 61 | — | COOMe | 4-MeO-benzyl | 6-MeO-3-pyridyl | 119–21 |
| 62 | — | COOMe | Me | 2-pyridyl | 80–2 |
| 63 | — | COOMe | H | 2-MeO-4-pyridyl | 132–5 |
| 64 | — | COOMe | H | 5,6-dichloro-3-pyridyl | 161–2 |
| 65 | — | COO⁻N⁺Bu₄ | H | 6-MeO-3-pyridyl | 250–2 |
| 66 | — | COOMe | H | 2-Cl-3-pyridyl | 120–1 |
| 67 | — | COOMe | H | 2-MeO-3-pyridyl | 78–81 |
| 68 | — | CH=N—OH | H | 6-MeO-3-pyridyl | 145–6 |
| 69 | — | C=N—NMe₂<br>\|<br>Me | H | 6-MeO-3-pyridyl | 87–9 |
| 70 | — | COOMe | H | 2-MeS-3-pyridyl | 117–9 |
| 71 | — | COOMe | H | 5-Br-6-MeO-3-pyridyl | 164–5 |
| 72 | — | COOMe | Me | 5-Br-6-MeO-3-pyridyl | 112–4 |
| 73 | — | COOMe | H | 5-MeO-2-pyridyl | 141–3 |
| 74 | — | COOMe | H | 6-Me-3-pyridyl | 125–6 |
| 75 | 5-Me | COOMe | H | 2-MeO-3-pyridyl | 139–40 |
| 76 | — | COOC₅H₁₁ | H | 6-MeO-3-pyridyl | 49–52 |
| 77 | — | COOCH₂—COOMe | H | 6-MeO-3-pyridyl | 125–7 |
| 78 | — | COOCH₂—C≡CH | H | 6-MeO-3-pyridyl | 129–32 |
| 79 | — | COOBuⁱ | H | 6-MeO-3-pyridyl | 81–3 |
| 80 | — | COOMe | H | 5-Ph-6-MeO-3-pyridyl | 159–61 |
| 81 | — | COOMe | —CH₂COOMe | 6-MeO-3-pyridyl | oil |
| 82 | — | COObenzyl | H | 2-MeO-3-pyridyl | 79–80 |
| 83 | — | C=N—OMe<br>\|<br>Me | Me | 6-MeO-3-pyridyl | oil |
| 84 | — | 5-(4-Cl-Ph)-1,3,4-oxadiazol-2-yl | H | 6-MeO-3-pyridyl | 193–7 |
| 85 | — | cyclohexyl<br>\|<br>COO⁻N⁺H₂<br>\|<br>cyclohexyl | H | 6-MeO-3-pyridyl | 203–5 |
| 86 | 4-F,5-Me | COOMe | H | 2-MeO-3-pyridyl | glass |
| 87 | — | 2-furyl | H | 6-MeO-3-pyridyl | 112–7 |
| 88 | — | COOCH₂—CH₂Cl | H | 6-MeO-3-pyridyl | 155–8 |
| 89 | — | COOMe | Me | 2-MeO-3-pyridyl | oil |
| 90 | 5-F | COOMe | H | 6-MeO-3-pyridyl | 125–6 |
| 91 | — | COOMe | allyl | 6-MeO-3-pyridyl | oil |
| 92 | — | COOMe | acetyl | 6-MeO-3-pyridyl | oil |
| 93 | — | COOMe | benzoyl | 6-MeO-3-pyridyl | 117–8 |
| 94 | — | COOMe | 3,4-MeO₂—Ph—CH₂CH₂— | 6-MeO-3-pyridyl | 116–8 |
| 95 | — | COOMe | H | 5-MeO-3-pyridyl | 117–9 |
| 96 | — | COOMe | —CH₂Ph | 5-Cl-6-MeO-3-pyridyl | 126–8 |
| 97 | — | COOMe | Me | 5,6-Cl₂-3-pyridyl | 103–4 |
| 98 | — | COOMe | H | 5-Cl-6-MeS- | 167–9 |

-continued

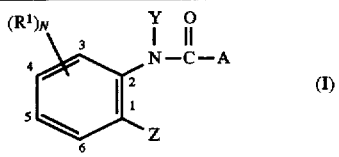

(I)

| Cpd | $(R^1)_n$ | Z | Y | A | m.p.(°) |
|---|---|---|---|---|---|
| 99 | — | COOMe | H | 5-Br-3-pyridyl | 122–3 |
| 100 | — | 5-(4-Cl—Ph)-1,3,4-oxadiazol-2-yl | Me | 6-MeO-3-pyridyl | 188–91 |
| 101 | — | COOMe | Me | 4,6-(MeO)$_2$-2-pyrimidinyl | 111–3 |
| 102 | 4-Me | COOMe | H | 6-MeO-3-pyridyl | 116–9 |
| 103 | — | COOMe | Me | 5-MeO-2-pyridyl | 82–4 |
| 104 | 5-Me | COOMe | H | 6-MeO-3-pyridyl | 160–2 |
| 105 | — | COOMe | Me | 5-MeO-3-pyridyl | 60–2 |
| 106 | 6-Cl | COOMe | H | 6-MeO-3-pyridyl | 160–2 |
| 107 | — | COOMe | H | 5,6-(MeO)$_2$-3-pyridyl | 155–7 |
| 108 | — | 5-(4-Cl—Ph)-1,3,4-thiadiazol-2-yl | H | 6-MeO-3-pyridyl | 215–7 |
| 109 | 4-Cl | COOMe | H | 2-(MeSO$_2$)-5-pyrimidinyl | 183–5 |
| 110 | 5-NO$_2$ | COOMe | H | 6-MeO-3-pyridyl | 197–9 |
| 111 | 3,5-Me$_2$ | COOMe | H | 6-MeO-3-pyridyl | 131–3 |
| 112 | — | COOMe | SO$_2$Me | 6-MeO-3-pyridyl | 125–8 |
| 113 | — | COOMe | H | 4-MeO-2-MeSO$_2$-5-pyrimidinyl | 187–90 |
| 114 | — | 1-pyrrolyl | H | 6-MeO-3-pyridyl | 113–6 |
| 115 | 4-Cl | COOMe | H | 2-MeO-5-pyrimidinyl | 175–7 |
| 116 | 6-F | COOMe | H | 6-MeO-3-pyridyl | 177–9 |
| 117 | 4-MeO | COOMe | H | 6-MeO-3-pyridyl | 164–5 |
| 118 | — | COOMe | —CH(Me)Ph | 6-MeO-3-pyridyl | 132–3 |
| 119 | — | COOMe | Me | 5,6-(MeO)$_2$-3-pyridyl | 110–2 |
| 120 | — | COOMe | H | 4-Cl-6-[N-(2-MeOCO—Ph)NHCO]-2-pyridyl | 210–2 |
| 121 | — | COOMe | H | 4-MeO-6-[N-(2-MeO—CO—Ph)NHCO]-2-pyridyl | 195–9 |
| 122 | — | COOMe | H | 6-[N-(2-MeOCO—Ph)—NHCO]-3-pyridyl | 198–200 |
| 123 | — | COOMe | H | 6-CF$_3$CH$_2$O-3-pyridyl | 173–4 |
| 124 | — | COOMe | H | 2,5-(MeO)$_2$-6-[N-(2-MeOCO—Ph)NHCO]-3-pyridyl | 195–9 |
| 125 | — | COOMe | H | 4,6-(EtO)$_2$-2-pyridyl | 115–6 |
| 126 | — | COOMe | 2-Me-benzyl | 2-MeO-3-pyridyl | 101–3 |
| 127 | 5-NH$_2$ | COOMe | H | 6-MeO-3-pyridyl | 171–3 |
| 128 | — | COOMe | H | 6-(2,3,4-Cl$_3$-1-pyrrolyl)-3-pyridyl | 183 |
| 129 | — | 2-benz-imidazolyl | H | 6-MeO-3-pyridyl | 272–5 |
| 130 | — | COO-allyl | H | 5-Cl-6-MeO-3-pyridyl | 113–5 |
| 131 | — | COOCH$_2$—C≡CH | H | 5-Cl-6-MeO-3-pyridyl | 163–5 |
| 132 | 3-F | COOMe | H | 6-MeO-3-pyridyl | 107–9 |
| 133 | 5-OH | COOMe | H | 6-MeO-3-pyridyl | 203–5 |
| 134 | 5-I | COOMe | H | 6-MeO-3-pyridyl | 154–6 |
| 135 | 5-MeOCO | COOMe | H | 6-MeO-3-pyridyl | 155–6 |
| 136 | 5-MeCONH | COOMe | H | 6-MeO-3-pyridyl | 253–6 |
| 137 | — | COOMe | —CH(Me)—COOMe | 6-MeO-3-pyridyl | 134–5 |
| 138 | — | COOMe | 2-Me-benzyl | 5-Cl-6-MeO-3-pyridyl | oil |
| 139 | — | COOEt | H | 5-Cl-6-MeO-3-pyridyl | 136–8 |
| 140 | — | COOH | H | 5-Cl-6-MeO-3-pyridyl | 247–50 |
| 141 | 5-MeSO$_2$NH | COOMe | H | 6-MeO-3-pyridyl | 184–5 |
| 142 | — | COOMe | H | 5-cyano-3-pyridyl | 190–2 |
| 143 | — | COOMe | H | 6-formyl-3-pyridyl | 153–7 |

-continued

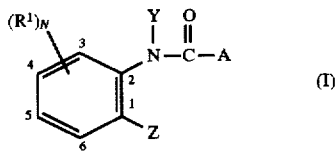

(I)

| Cpd | (R¹)ₙ | Z | Y | A | m.p.(°) |
|---|---|---|---|---|---|
| 144 | — | COOMe | H | 5-Br-2-MeO-3-pyridyl | 180–2 |
| 145 | 4-Cl | COOMe | Me | 2-MeO-5-pyrimidinyl | 86–8 |
| 146 | — | COOMe | H | 2-Cl-4-pyridyl | 108–10 |
| 147 | — | COOMe | H | 2-Cl-6-MeO-3-pyridyl | 144–5 |
| 148 | — | COOMe | H | 6-(2,3,4,5-Cl₄-1-pyrrolyl)-3-pyridyl | 289 |
| 149 | — | COONa | H | 6-Cl-3-pyridyl | 300 |
| 150 | — | COOMe | H | 6-MeOCH₂-3-pyridyl | 117–8 |
| 151 | — | COOMe | H | 5-cyano-6-MeO-3-pyridyl | 247–50 |
| 152 | — | 5-Me-1,3,4-thiadiazol-2-yl | H | 6-MeO-3-pyridyl | 143–5 |
| 153 | — | COOMe | H | 5-cyano-6-Me₂N-3-pyridyl | 190–2 |
| 154 | — | COOMe | H | 5-MeSO₂O-3-pyridyl | 149–51 |
| 155 | — | COOMe | H | 6-(2,3,5-Cl₃-1-pyrrolyl)-3-pyridyl | 134–5 |
| 156 | — | COOMe | H | 6-MeOCO-3-pyridyl | 141 |
| 157 | — | COOMe | H | 5-PhCH₂O-3-pyridyl | 123–31 |
| 158 | — | COOMe | H | 5-MeS-3-pyridyl | 122–3 |
| 159 | — | COOMe | H | 5-MeOCO-2-pyridyl | 187–8 |
| 160 | — | COOMe | H | 2,6-(MeO)₂-3-pyridyl | 141–3 |
| 161 | — | COOMe | H | 5-MeSO₂-3-pyridyl | 168–70 |
| 162 | — | COOMe | H | 5-MeSO-3-pyridyl | 130–2 |
| 163 | — | COOMe | Me | 5-MeS-3-pyridyl | oil |
| 164 | — | COOMe | H | 5-(N≡C—CH₂O)-3-pyridyl | solid |
| 165 | — | COOMe | Me | 5-MeSO₂-3-pyridyl | 109–11 |
| 166 | — | COOMe | H | 5-ClCH₂S-3-pyridyl | 112–4 |
| 167 | — | COOH | H | 6-Cl-3-pyridyl | 240 |
| 168 | — | COOMe | H | 5-MeOCO-3-pyridyl | 147–8 |
| 169 | — | COOMe | H | 6-[N-(2-MeOCO—Ph)—NHCO]-3-pyridyl | 195–9 |
| 170 | — | COOMe | H | 5-Me-3-pyridyl | 116–7 |
| 171 | — | COOMe | H | 6-MeO-5-NO₂-3-pyridyl | 150–1 |
| 172 | — | COOMe | H | 6-PhO-3-pyridyl | 97–8 |
| 173 | — | COOMe | H | 5,6-(MeS)₂-3-pyridyl | 157–8 |
| 174 | — | COOMe | Me | 2,6-(MeO)₂-3-pyridyl | 103–5 |
| 175 | — | COOMe | Me | 5-MeOCO-3-pyridyl | oil |
| 176 | — | COOMe | Me | 5-Me-3-pyridyl | 114–5 |
| 177 | — | COOH | H | 5-HOCO-3-pyridyl | 275 |
| 178 | — | COOMe | H | 5-acetyl-6-Me-3-pyridyl | 144–5 |
| 179 | — | COOMe | H | 5-Ph-3-pyridyl | 124–5 |
| 180 | — | COOMe | Me | 6-PhO-3-pyridyl | 114–5 |
| 181 | — | COOMe | H | 5-[N-(2-MeOCO—Ph)—NHCO]-3-pyridylthio | 180–2 |
| 182 | — | COOMe | H | 5-PhCH₂S-3-pyridyl | 104–6 |
| 183 | — | COOMe | Me | 5-MeO-2-pyrazinyl | 81–3 |
| 184 | 4-F | COOMe | Me | 6-MeO-3-pyridyl | 102–4 |
| 185 | — | COOMe | Et | 6-MeO-3-pyridyl | 53–5 |
| 186 | — | COOMe | H | 2-MeO-5-pyrimidinyl | 164–5 |
| 187 | — | COOMe | Me | 2-MeO-5-pyrimidinyl | 128–30 |
| 188 | — | COOMe | H | 4,6-(MeO)₂-2-PhCH₂O-5-pyrimidinyl | 127–9 |
| 189 | — | COOMe | H | 2-Cl-4CF₃-5-pyrimidinyl | 139–40 |
| 190 | — | COOMe | H | 2-Me₂N-4CF₃-5-pyrimidinyl | 133–6 |
| 191 | — | COOMe | H | 2-MeO-4CF₃-5-pyrimidinyl | 13940 |
| 192 | — | COOMe | H | 6-Cl-5-MeO- | 168–71 |

-continued

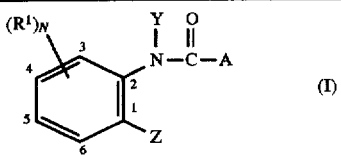

(I)

| Cpd | (R¹)ₙ | Z | Y | A | m.p.(°) |
|---|---|---|---|---|---|
| 193 | — | COOMe | H | 2-pyrazinyl | 165–6 |
| | | | | 5-Br-2-Me-4-pyrimidinyl | |
| 194 | — | COOMe | H | 2,4,6-(MeO)₃-5-pyrimidinyl | 153–5 |
| 195 | — | COOMe | Me | 6-Cl-3-pyridyl | 84–6 |
| 196 | — | COOMe | H | 2-Cl-4-pyrimidinyl | 159–61 |
| 197 | — | COOMe | H | 5-Me-2-pyrazinyl | 158–60.5 |
| 198 | — | COOMe | H | 2-MeO-4-pyrimidinyl | 135–6 |
| 199 | — | COOPr | H | 2-MeSO₂-5-pyrimidinyl | 129–31 |
| 200 | — | COOPr | H | 2-MeSO-5-pyrimidinyl | 116–8 |
| 201 | — | COOPr | H | 2-MeO-5-pyrimidinyl | 104–5 |
| 202 | — | COOEt | H | 2-EtO-5-pyrimidinyl | 134–5 |
| 203 | — | COOH | H | 2-EtO-5-pyrimidinyl | 150–62 |
| 204 | — | COOMe | H | 2-Me-5-pyrimidinyl | 141–3 |
| 205 | — | COOMe | H | 5-pyrimidinyl | 158–61 |
| 206 | — | COOMe | Me | 2-Me-5-pyrimidinyl | 88–90 |
| 207 | — | COOMe | H | 2-Cl-5-pyrimidinyl | 159–61 |
| 208 | — | COOMe | H | 2-Br-5-pyrimidinyl | 177–8 |
| 209 | — | COOMe | H | 2-PhCH₂NH-5-pyrimidinyl | 192–4 |
| 210 | — | COOMe | H | 2-morpholino-5-pyrimidinyl | 222–3 |
| 211 | — | COOMe | H | 5-Br-2-MeS-4-pyrimidinyl | 192–4 |
| 212 | — | COOMe | H | 5-Br-2-MeO-4-pyrimidinyl | 178–80 |
| 213 | — | COOMe | H | 2-MeOCOCH₂NH-5-pyrimidinyl | 194–7 |
| 214 | — | COOMe | H | 2,6-Cl₂-4-pyrimidinyl | 170–5 |
| 215 | — | COOMe | H | 2-CF₃-5-pyrimidinyl | 143–5 |
| 216 | — | COOMe | H | 2-Ph-5-pyrimidinyl | 151–5 |
| 217 | — | COOMe | H | 2,6-(MeO)₂-4-pyrimidinyl | 167–9 |
| 218 | — | COOMe | Me | 2-Ph-5-pyrimidinyl | gum |
| 219 | — | COOMe | H | 2,6-Cl₂-5-pyrimidinyl | 135–7 |
| 220 | — | COOMe | H | 2-NC-5-pyrimidinyl | 186–8 |
| 221 | — | COOMe | H | 4,5-(MeO)₂-2-pyrimidinyl | 182–3 |
| 222 | — | COOMe | H | 4,6-(MeO)₂-2-pyrimidinyl | 163–4 |
| 223 | — | COOMe | H | 2-MeONH-5-pyrimidinyl | 194–6 |
| 224 | — | COOMe | H | 2-MeNH-5-pyrimidinyl | 230–1 |
| 225 | — | COOMe | H | 2-Cl-4-(2-MeOCO—PhNH)-5-pyrimidinyl | 190–2 |
| 226 | — | COOMe | H | 5-Cl-6-Me-2-pyrazinyl | 136–41 |
| 227 | — | COOMe | H | 5-MeO-6-Me-2-pyrazinyl | 166–9 |
| 228 | — | COOMe | H | 2-(N-methoxy-N-methoxycarbonyl-amino)-5-pyrimidinyl | 151–2 |
| 229 | — | COOMe | H | 2-cyclopropyl 5-pyrimidinyl | 112–4 |
| 230 | 3-MeOCO | COOMe | H | 6-MeO-3-pyridyl | 111–4 |
| 231 | — | COOMe | H | 2-MeS-5-pyrimidinyl | 160–2 |
| 232 | — | COOMe | H | 5,6-Cl₂-2-pyrazinyl | 143–8 |
| 233 | — | COOMe | H | 5-(2-thienyl)-3-pyridyl | 148–9 |
| 234 | — | COOMe | H | 5-(4-CF₃—Ph)-3-pyridyl | 155–6 |
| 235 | — | COOMe | H | 5-(ClSO₂)-3-pyridyl | 144–5 |
| 236 | — | COOMe | H | 5-(Cl₂CHS)-3-pyridyl | 120–2 |

-continued

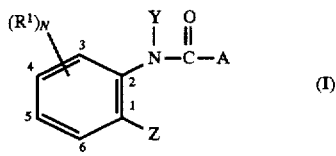

(I)

| Cpd | (R¹)ₙ | Z | Y | A | m.p.(°) |
|---|---|---|---|---|---|
| 237 | — | COOMe | H | 5-(NH₂SO₂)-3-pyridyl | 185–7 |
| 238 | — | COOMe | H | 5-Br-6-Cl-3-pyridyl | 157–9 |
| 239 | — | COOMe | Me | 5-NO₂-6-MeO-3-pyridyl | 98–100 |
| 240 | — | COOMe | H | 2-(1-imidazolyl)-5-pyrimidinyl | 193–5 |
| 241 | — | COOMe | H | 4-MeO-2-MeS-5-pyrimidinyl | 140–2 |
| 242 | — | COOMe | Me | 2,6-(MeO)₂-4-pyrimidinyl | 101–3 |
| 243 | — | COOH | 3,4-(MeO)₂-benzyl | 6-MeO-3-pyridyl | 123–4 |
| 244 | — | COOMe | H | 5-(Me₂NSO₂)-3-pyridyl | 169–70 |
| 245 | — | COOMe | H | 5-Br-6-MeO-3-pyridyl | 169–70 |
| 246 | — | COOMe | H | 5-Br-6-MeSO₂-3-pyridyl | 223–5 |
| 247 | — | COOMe | H | 5-Br-6-MeSO-3-pyridyl | 160–2 |
| 248 | — | COOC₅H₁₁ | H | 2-MeO-3-pyridyl | 47–8 |
| 249 | — | COO-allyl | H | 2-MeO-3-pyridyl | 80–1 |
| 250 | — | COOMe | 2-Me-benzyl | 6-(2-Me-benzyl)-3-pyridyl | oil |
| 251 | — | COOMe | H | 2-Cl-4-quinolinyl | 163–4 |
| 252 | — | COOMe | —CH₂Ph | 6-MeO-3-pyridyl | 101–2 |
| 253 | 4,5-MeO₂ | COOMe | H | 2-MeO-3-pyridyl | 152–4 |
| 254 | — | COOMe | H | 5-NH₂-6-MeO-3-pyridyl | 202–3 |
| 255 | — | COOMe | Me | 2,4-(MeO)₂-5-pyrimidinyl | 78–81 |
| 256 | — | COOMe | 2-MeO-benzyl | 2-MeO-5-pyrimidinyl | gum |
| 257 | — | COOMe | H | 4-Me-2-MeS-5-pyrimidinyl | 78–81 |
| 258 | — | COOMe | H | 2-(3-pyridyloxy)-5-pyrimidinyl | 124–6 |
| 259 | — | COOMe | H | 2-F-3-pyridyl | 130–1 |
| 260 | — | COOMe | 2-Me-benzyl | 5,6-(MeO)₂-3-pyridyl | oil |
| 261 | — | COOMe | H | 5,6-methylenedioxy-3-pyridyl | 168–79 |
| 262 | — | COOMe | H | 5-I-6-MeO-pyridyl | 173–5 |
| 263 | 3,4-Me₂ | COOMe | H | 2-MeO-3-pyridyl | 126–7 |
| 264 | 4-Cl | COOMe | H | 2-MeO-3-pyridyl | 128–30 |

The following compounds were also prepared a) ethyl N-(6-methoxy-3-pyridinethiocarbonyl)anthranilate, as an oil, (compound 265)

b) methyl N-(5,6-dimethoxy-3-pyridinethiocarbonyl)-anthranilate, m.p. 154–5°, (compound 266)

c) methyl N-(2-methoxy-5-pyrimidinethiocarbonyl)-anthranilate, m.p. 135–7°, (compound 267)

d) isobutyl N-(6-methoxy-3-pyridinethiocarbonyl)-anthranilate, as an oil, (compound 268)

Test Example

Compounds are assessed for activity against one or more of the following:

*Phytophthora infestans*: late tomato blight
*Plasmopara viticola*: vine downy mildew
*Erysiphe graminis*: barley powdery mildew
*Pyricularia oryzae*: rice blast
*Pellicularia sasakii*: rice sheath blight
*Botrytis cinerea*: grey mould
*Venturia inaequalis*: apple scab
*Leptosphaeria nodorum*: glume blotch Aqueous solutions or dispersions of the compounds at the desired concentration, including a wetting agent, were applied by spray or by drenching the stem base of the test plants, as appropriate. Plants or plant parts were then inoculated with appropriate test pathogens and kept under controlled environment conditions suitable for maintaining plant growth and development of the disease. After an appropriate time, the degree of infection of the affected part of the plant was visually estimated. Compounds were considered active if they gave greater than 50% control of the disease at a concentration of 500 ppm (w/v) or less.

Compounds 28, 38, 41, 50, 98, 101, 155, 216 and 260 showed activity against *Phytophthora infestans*; Compounds 9, 28, 36, 37, 49–51, 54, 56, 59, 61, 66, 67, 70, 71, 83, 98, 101, 111, 113, 114, 116, 120, 121, 137, 139, 142, 156, 161, 174–178, 184, 187, 208, 222, 223, 235, 240–242, 245 and 251 showed activity against *Plasmopara viticola;* Compounds 1–3, 9–12, 20, 23, 25–27, 29–31, 34, 35, 44, 46, 54, 58, 61, 63, 71, 72, 78, 79, 90–94, 96, 99, 101, 106–108, 116, 119, 130, 131, 139, 151, 152, 171, 174, 183–187, 192, 202, 213, 217, 223, 224, 226–228, 232, 239, 242, 245–247, 249, 250, 252 and 260 showed activity against *Erysiphe graminis;*

Compounds 1, 1a, 2, 6a, 42, 43, 48, 57, 59, 62, 64, 65, 110, 113, 144, 146, 172, 204, 206, 223 and 251 showed activity against *Pyricularia oryzae;* Compounds 14, 39, 43, 54, 100, 101, 185, 189, 190 and 252 showed activity against *Pellicularia sasakii;* Compounds 42, 45–47, 53, 55, 106, 113, 170, 202 and 225 showed activity against *Botrytis cinerea;* Compounds 1, 8, 12, 17, 40, 55, 74, 90, 98, 104, 127, 129, 162, 164, 178, 185, 193, 198, 213, 218, 219, 222 and 224 showed activity against *Venturia inaequalis;* and Compounds 33, 52, 53, 178, 190, 194 and 223 showed activity against *Leptosphaeria nodorum.*

We claim:

1. A compound of the formula

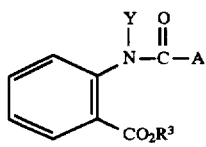

in which A is 6-alkoxy-3-pyridyl, optionally substituted by halogen; Y is hydrogen or alkyl; and $R^3$ is alkyl or a metal salt complex thereof.

2. A compound of claim 1 in which the alkoxy is methoxy and Y is hydrogen or methyl.

3. A compound according to claim 2 in which $R^3$ is $C_{1-6}$ alkyl.

4. A compound according to claim 3 in which $R^3$ is ethyl and Y is hydrogen.

5. A compound according to claim 3 in which $R^3$ is isopropyl and Y is hydrogen.

6. A compound according to claim 1 in which A is 6-methoxy-3-pyridyl.

7. A compound according to claim 1 in which A is 5-chloro-6-methoxy-3-pyridyl.

8. A fungicidal composition which comprises a compound according to claim 1 in admixture with an agriculturally acceptable diluent or carrier.

9. A fungicidal composition which comprises a compound according to claim 3 in admixture with an agriculturally acceptable diluent or carrier.

10. A fungicidal composition which comprises a compound according to claim 6 in admixture with an agriculturally acceptable diluent or carrier.

11. A fungicidal composition which comprises a compound according to claim 7 in admixture with an agriculturally acceptable diluent or carrier.

12. A method of combatting cytopathogenic fungi at a locus infested or liable to be infested therewith, which comprises applying to the locus an effective amount of a compound as claimed in claim 1.

13. A method of combatting cytopathogenic fungi at a locus infested or liable to be infested therewith, which comprises applying to the locus an effective amount of a compound as claimed in claim 3.

14. A method of combatting cytopathogenic fungi at a locus infested or liable to be infested therewith, which comprises applying to the locus an effective amount of a compound as claimed in claim 6.

15. A method of combatting cytopathogenic fungi at a locus infested or liable to be infested therewith, which comprises applying to the locus an effective amount of a compound as claimed in claim 7.

16. Fungicidal composition which comprises a compound as claimed in claim 1 in admixture with an agriculturally acceptable diluent or carrier.

17. A method of combating phytopathogenic fungi at a locus an effective amount of infested or liable to be infested therewith, which comprises applying to the locus a compound as claimed in claim 1.

* * * * *